United States Patent [19]

Quaranta et al.

[11] Patent Number: 5,344,919
[45] Date of Patent: Sep. 6, 1994

[54] INTEGRIN FROM HUMAN EPITHELIAL CELLS

[75] Inventors: Vito Quaranta, La Jolla, Calif.; Shama Kajiji, Mystic, Conn.

[73] Assignee: The Scripps Research Institute, La Jolla, Calif.

[21] Appl. No.: 14,090

[22] Filed: Feb. 4, 1993

Related U.S. Application Data

[63] Continuation of Ser. No. 293,384, Jan. 4, 1989, abandoned, which is a continuation-in-part of Ser. No. 16,552, Feb. 19, 1987, abandoned.

[51] Int. Cl.$^5$ ............................................. C07K 15/14
[52] U.S. Cl. ................................... 530/395; 530/350; 530/403
[58] Field of Search ................. 530/350, 395, 403; 424/88

[56] References Cited

FOREIGN PATENT DOCUMENTS 0154550 9/1985 European Pat. Off. .
3329184 2/1985 Fed. Rep. of Germany .

OTHER PUBLICATIONS

Kennel et al. (1981) Cancer Res. 41, 3465–3470.
Falcioni et al. (1986) Cancer Res. 46, 5772–5778.
Kennel et al. (1986) Cancer Res. 46, 707–712.
Kennel (1989) J. Biol. Chem. 264, 15515–15521.
Hemler et al. (1989) J. Biol. Chem. 264, 6529–6535.
Ruoslahti et al. (1987) Science 238, 491–497.
Suzuki et al. (1986) Proc. Natl. Acad. Sci. 83, 8614–8618.
Springer et al. (1985) Nature 314, 540–542.
Hynes (1987) Cell 48, 549–554.
Schmiegel et al., (1985) Cancer Research, 45:1402–1407.
Maimonis et al. (1985) Hybridoma 4:77.
Metzgar et al. (1982) Cancer Research 42:601–608.
Usui et al. (1985) Biological Abstracts 80:AB–587.
Schmiegel et al., (1985) Chemical Abstracts, 45:1402–1407.
Kajiji et al. (1987) Cancer Research 47:1367–1376.
Sonnenberg et al. (1986) J. Histochem. Cytomchem. 34:1037–1046.
Kennel et al. (1986) Cancer Research 46:707–712.

Primary Examiner—Keith Baker
Attorney, Agent, or Firm—Thomas Fitting

[57] ABSTRACT

Novel hybridoma cell lines producing monoclonal antibodies which react specifically with human pancreatic cancer cells are described. Methods for producing antigenic preparations to generate the hybridoma cell lines and for selecting, purifying and characterizing the monoclonal antibodies reactive with human cells, including pancreatic cancer cells, are disclosed. The antigens to which the antibodies of the invention are specific are characterized.

1 Claim, 3 Drawing Sheets

INTEGRIN FROM HUMAN EPITHELIAL CELLS

This is a continuation of copending application Ser. No. 07/293,384 filed on Jan. 4, 1989, now abandoned, which is a continuation-in-part of U.S. Ser. No. 016,552, filed Feb. 19, 1987, by Kajiji and Quafanta, which is now abandoned and incorporated herein by reference.

BACKGROUND OF THE INVENTION

The present invention relates generally to a novel antigen and to novel hybridoma cell lines, and more specifically to monoclonal cell lines producing monoclonal antibodies reactive with the novel antigen, which antigen can be found on human pancreatic cancer cells.

Cancer currently constitutes the second most common cause of death in the United States. Carcinomas of the pancreas are the eighth most prevalent form of cancer and fourth among the most common causes of cancer deaths in this country. The incidence of pancreatic cancer has been increasing steadily in the past twenty years in most industrialized countries, exhibiting the characteristics of a growing epidemiological problem.

The prognosis for pancreatic carcinoma is, at present, very poor, it displays the lowest five-year survival rate among all cancers. Such prognosis results primarily from delayed diagnosis, due in part to the fact that the early symptoms are shared with other more common abdominal ailments. The diagnosis of pancreatic cancer is often dependent on exploratory surgery, inevitably performed after the disease has advanced considerably.

Substantial efforts have been directed to developing tools useful for early diagnosis of pancreatic and other carcinomas. Nonetheless, a definitive diagnosis is often dependent on exploratory surgery which is inevitably performed after the disease has advanced past the point when early treatment may be effected. One promising method for early diagnosis of various forms of cancer is the identification of specific biochemical moieties, termed antigens present on the surface of cancerous cells. Antibodies which will specifically recognize and bind to the antigens present on the surfaces of cancer cells potentially provide powerful tools for the diagnosis and treatment of the particular malignancy. Tumor specific cell surface antigens have previously been identified for certain melanomas, lymphomas malignancies of the colon and reproductive tract.

There thus exists a great and long-felt need for a cell surface marker which is present on the surface of neoplastic cells, including those of the pancreas, and for antibodies which specifically recognize such a cell surface marker. Such markers and corresponding antibodies would be useful not only in the early detection of pancreatic and other cancers, but in their treatment as well. The present invention satisfies these needs and provides related advantages as well.

Cell adhesion is critical to many biological processes, including embryonal development, tissue repair, immune response, and malignant transformation. (Ekblom, P., et al. (1986) *Ann. Rev. Cell. Biol.* 2:27–47; Yamada, K. M. (1983) *Ann. Rev. Biochem.* 52:761–799; Edelman, G. M. (1983) *Science* 219:450–457.) Several laboratories have recently done biochemical characterization of adhesion receptors for extracellular matrix and plasma proteins such as fibronectin and vitronectin as well as leukocyte adhesion receptors. (Tamkun, J. W., et al. (1986) *Cell* 46:271–282; Damsky, C. H., et al. (1981) *J. Cell. Biol.* 89:173–184; Pytela, R., et al. (1985) *Cell* 40:191–198; Fitzgerald, L. A., et al. (1987) *J. Biol. Chem.* 262:3936–3939; Giancotti, F. G. (1985) *Ext. Cell Res.* 156:182–190; Springer, T. A. (1985) *Nature* 314:540–542.) These adhesion receptor proteins have been shown to be structurally homologous to each other. (Charo, I .F. (1986) *Proc. Natl. Acad. Sci. USA* 83:8351–8355; Suzuki, S. (1986) *Proc. Natl. Acad. Sci. USA* 83:8416–8418; Kishimoto, T. K. (1987) *Cell* 48:681–690; Takada, Y. (1987) *Nature* 326:607–609.) These related molecules have now been organized into a protein superfamily, designated "integrins", after the chicken fibronectin/laminin receptor. (Hynes, R. O. (1987) *Cell* 48:549–554.)

SUMMARY OF THE INVENTION

The present invention provides monoclonal antibodies characterized in that the antibodies react specifically to human pancreatic carcinoma (HPC) cells. These monoclonal antibodies, which recognize and bind to cell surface markers in HPC cells, may be advantageously used for diagnosis and treatment of HPC.

In accordance with the present invention there are provided monoclonal antibodies which react specifically with antigenic markers on the surface of HPC cells. In accordance with a further aspect of the invention, there are provided hybridoma cell lines which produce monoclonal antibodies specifically reactive with HPC cell surface markers.

Preferred hybridoma cell lines are those termed S3-41 and S3-53 identified by ATCC accession numbers HB 9318 and HB 9319, respectively. The monoclonal antibodies produced and the antigens recognized by these cell lines are also a part of the present invention.

It will be appreciated from the foregoing that the present invention provides novel markers for antibodies against HPC tumor cells. In one aspect of the invention, the monoclonal antibodies are used for in vitro immunoassays to detect HPC. In another aspect of the invention, the monoclonal antibodies, conjugated with certain detectable labels, are useful as in vivo imaging agents for detecting HPC. Moreover, when conjugated with certain toxins, such monoclonal antibodies are useful for therapeutic treatment of HPC.

Another aspect of the invention concerns the cell surface markers reactive with the antibodies of the invention. These markers are useful in characterization of the cells bearing them and in design of agonists and antagonists of their functions. The antigens reactive with HB 9318 antibodies are members of the integrin super family.

The antigen reactive with HB 9318 is a new member of the integrin superfamily. As with other integrins, this molecule is a heterodimer comprised of structurally unrelated subunits, both of which are glycosylated. That this integrin, isolated from human epithelial cells, is novel was shown by amino acid sequence homologies. No obvious serologic cross-reactivities were detected with other integrins. The $\beta$-chain of the epithelial integrin has a molecular weight which is significantly higher than other integrin $\beta$-chains. It is postulated that this is due to a large sialic acid content.

Because integrin heterodimers are grouped into three families, based upon which of the three $\beta$-chains they contain, it is proposed that the $\beta$-chain of the present invention be designated $\beta 4$ in recognition of its defining a fourth integrin $\beta$-chain family.

Other features and advantages of the present invention will become apparent from the following detailed description which illustrates, by way of example, the principles of the invention.

DETAILED DESCRIPTION OF THE PREFERRED EMBODIMENT

I. DEFINITIONS

Figure 1:
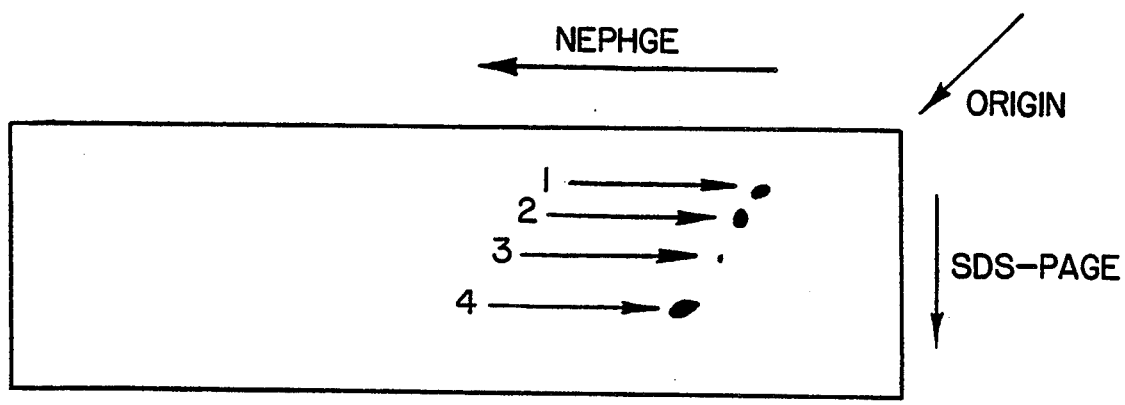
FIG. 1 shows two-dimensional gel analysis of immunoprecipitates obtained by reacting HB 9318 with radiolabeled extracts of FG cells.

"Monoclonal antibodies (Mabs) reactive with HPC" refers to homogenous populations of immunoglobulins which are capable of immunoreaction with antigens expressed on human pancreatic cancer (HPC) cells. It is understood that there may be a number of antigens present on the surface of any cell and, alternatively, that certain receptors present on HPC cells may also occur on other malignant or normal cell types. Moreover, such antigens may, in fact, have a number of antigenic determinants. The antibodies of the invention may be directed against one or more of these determinants. Any characteristic antigen associated with HPC may provide the requisite antigenic determinant.

Immunoglobulins, like all proteins, may exist in acidic, basic or neutral form depending on their amino acid composition and environment, and may be found in association with other molecules such as saccharides or lipids. The immunoglobulins of the present invention fall within the definition regardless of status in this regard as long as they remain capable of selectively reacting with HPC associated antigens.

"Cells" or "cell line" refers to the cells apparently denoted as well as the progeny thereof. It is known that during cell multiplication and growth cells or cell lines may not remain precisely constant in their genetic makeup and the progeny may, indeed, be distinguishable in some way from the parent cells. So long as the cells referred to herein retain the characteristic of secretion capability for Mabs reactive with HPC, as defined above, they are to be considered included in the definition.

"Immortalizing cell line" refers to a cell line which can be maintained perpetually, for practical purposes, in cell culture, i.e., for an indefinite number of transfers. It must also, when fused to an ordinary non-transformed cell line, which would normally not survive for more than a few days or weeks as a unicellular culture, be able to confer on the fusion product its own immortal properties.

II. HYBRIDOMA PREPARATION

A. GENERAL DESCRIPTION OF HYBRIDOMA PREPARATION

The examples below describe the preparation of specific hybridoma cell lines producing monoclonal antibodies reactive with HPC cell antigens. It will be appreciated, however, that alternative methods may be employed to obtain alternative embodiments of the specific Mabs reactive with HPC cell antigens.

Techniques for preparing hybridomas are generally well-known in the art. Generally speaking, such hybridoma cell lines are prepared by a process involving the fusion under appropriate conditions of an immortalizing cell line and a B lymphocyte cell line appropriately immunized to produce the desired antibody. While the immortalizing cell lines so used are often of murine origin, those of any other mammalian species may be employed alternatively including those of rat, bovine, canine, human origin and the like. The immortalizing cell lines are most often of tumor origin, particularly myeloma cells, but may also include normal cells transformed with, for example, Epstein Bart Virus. Any immortalizing cell here may be used to prepare the hybridomas of the present invention.

Cells capable of secreting antibodies were employed as fusion partners, such as spleen cells or peripheral blood lymphocytes. The animal from which the cells were to be derived was immunized at intervals with whole cell suspensions of human pancreatic cancer cells. Alternatively, cell extracts or purified antigen may be used for immunization.

The immortalizing cells and lymphold cells were fused to form hybridomas according to standard and well-known techniques employing polyethylene glycol as a fusing agent. Alternatively fusion may be accomplished by electrofusion. Hybridomas are screened for appropriate monoclonal antibody secretion by assaying the supernatant or protein purified from the ascites for reactivity with the desired cell or antigen. Such assay techniques include, among others, ELISA, RIA Western Blotting, or immunoprecipitation.

In the present invention, hybridomas were initially screened for production of antibodies reactive with HPC cells. Alternatively, HPC cell extracts or purified antigens could be used for screening. In order to further characterize the monoclonal antibodies, their reactivity with various HPC cell lines, other tumor cell lines and a variety of other normal, malignant and non-malignant pathological human tissues was determined using standard assay techniques such as ELISA, RIA, immunoprecipitation, histochemical staining procedures including indirect immunoperoxidase or indirect immunofluorescence staining. The hybridomas of the present invention were found to produce monoclonal antibodies generally highly reactive with all human pancreatic cell lines. They also displayed high reactivity with cells derived from other tumors, noticeably those of gastrointestinal and genitourinary tract origin. Moreover, although they displayed some reactivity with certain normal tissues, the Mab displayed negligible reactivity with major organs such as liver and kidney. Apparently, the antigens against which the antibodies are directed are highly expressed on HPC cells but only moderately or less on other cell types.

Because of their selective reactivity with HPC cell derived antigens the monoclonal antibodies are useful for both diagnosis and therapy of HPC and other carcinomas. Moreover, their non-reactivity with liver and kidney cells in particular permits them to be used therapeutically with relatively little risk of targeting these critical organs.

The antibodies of the invention are also useful in the preparation of cell surface markers reactive with them using immunoprecipitation and/or affinity chromatography of cell membrane preparations. The marker reactive with HB 9318 antibodies described below is a member of the integrin super family, and is functional in mediating binding to the extracellular matrix. Accordingly, this marker is involved in metastasis and colonization of malignant cells.

B. PARTICULAR HYBRIDOMA EMBODIMENTS

The following examples illustrate a method for preparing hybridomas which can serve as sources for the desired monoclonal antibodies, and the antibodies thus produced. While the methods described are typical of those which might be advantageously used, other alternative procedures known to those skilled in the art may be alternatively employed. The examples are thus intended to illustrate, but not to limit the invention.

EXAMPLE 1

PREPARATION OF HYBRIDOMA CELL LINE

Murine Mabs reactive with HPC cell lines were produced essentially according to the standard techniques of Kohler and Milstein, Nature 256:495 (1975). Briefly, standard HPC cell lines such as COLO 357 and its subclones were used to obtain the antigenic preparation. Preferably cells of the cell line termed FG were employed. (Kajiji, S. M., Intraneoplastic Diversity in Human Pancreatic Cancer, Ph.D. Thesis, Brown University (1984). Alternatively other pancreatic cell lines expressing the antigens may be used, such as BxPC-3 (ATCC No. CRL1687). The cells were grown in a monolayer culture and harvested by EDTA treatment. Briefly, confluent monolayers were incubated for 20 minutes at 37° C. with PBS containing 10 mM EDTA and 0.02% KCl. The detached cells were collected, centrifuged at 1000 ×g for 10 minutes and washed twice with cold PBS. Alternatively, cell suspensions were derived from FG xenografts grown in Balb/c athymic nude mice.

Two to four month old normal Balb/c mice were immunized with whole cell suspensions at weekly intervals with six intraperitoneal 0.5 ml injections, containing approximately $5 \times 10^6$ to $5 \times 10^8$ cells/injection/mouse. Three days after the final injection, the mice were sacrificed and the spleens removed. The spleens were placed in serum free Dulbecco's Minimal Essential Medium (DMEM) in separate Petri dishes and washed. The splenocytes were gently teased out of the fibrous splenic capsule using a rubber policeman. The cell suspension was then placed in a 15 ml tube and centrifuged at 1000 ×g for 10 minutes. The pellet was then washed twice with serum-free DMEM.

The washed spleen cells and the P3X63Ag8 myeloma cells were fused according to the method of Kohler and Milsrein, supra. The immortalized cell line fusion partners used were the murine myeloma cell line P3X63Ag8 (ATCC Accession No. T1B9) These myeloma cells were grown at a density of $5 \times 10^5$ cells/ml and harvested by centrifugation at 1000 ×g for 10 minutes. The cell pellet was washed twice with serum free DMEM. Finally, the spleen cells and the P3X63Ag8 myeloma cells were combined at a ratio of 7:1 in a 50 ml tube and pelleted by centrifugation (1000 g for 10 minutes). The pellet was gently loosened and 1 ml of a 35% polyethylene glycol (PEG) solution was gently bubbled over the cells. After 1 minute, 1 ml of DMEM, containing 10% fetal calf serum (FCS)(Gibco, Grand Island, N.Y.) was added to the cell suspension and gently mixed.

The PEG was subsequently diluted by the addition of 10 ml DMEM containing 10% FCS and the cells were repelleted. The cell pellet containing hybridoma fusion products was resuspended in 30 ml hypoxanthine-aminopterin-thymidine (HAT) medium (aminopterin from Sigma Chemical Co., St. Louis, Mo.; hypoxanthine and thymidine from Calbiochem, La Jolla, Calif.).

This cell suspension was then combined with 400 ml of HAT medium containing $2 \times 10^6$ thymocytes per ml (feeder cells). The contents were distributed into sterile 96 well plates (Costar, Cambridge, Mass.) and placed immediately in an incubator at 37° C. The spent media was replaced with fresh thymocyte containing HAT media after one week. Using this type of protocol successful hybridoma cultures were obtained which could be maintained with periodic addition of fresh DMEM containing 10% FCS.

Hybridomas producing monoclonal antibodies reactive with HPC cells were selected. After the cultures reached a cell density that covered 75–100% of the microtiter well surface, media from the hybridomas were screened for the presence of anti-HPC antibody, using a standard ELISA protocol. (Schultz, Cancer Res. 44:5914(1984)). Briefly, tumor dried onto the bottom of 96-well miniplates (Dynatech Microtiter Plates, American Scientific Products, McGaw Park, Ill.) were used as targets. The wells of antigen-coated 96 well plates to be used were rinsed with buffer A pH 8.0 (20 mM Tris, containing 150 mM NaCl, 0.2% Tween 20 and 0.01% Thimerosal). The hybridoma supernatant diluted 1:2 in buffer B (buffer A containing 0.1% bovine serum albumin) was added to the wells and incubated for 1 hour at room temperature to permit binding of specific antibodies. Specifically bound antibodies were detected by adding horseradish peroxidase-conjugated rabbit anti-mouse immunoglobulin (BioRad, Richmond, Calif.) to wells that were rinsed free of the excess hybridoma supernatant by washing with buffer A. After incubation for 1 hour at room temperature the secondary antibody was decanted, the wells washed with buffer A, and 50 $\mu$l/well of substrate solution (ten milliliters of 80 mM citrate phosphate buffer, pH 5.0 containing 4 mg O-phenylenediamine (Sigma Chem. Co., St. Louis, Mo.) and 4 $\mu$l 30% hydrogen peroxide) was added. The plates were incubated in the dark for 30 min at RT and the color reaction was stopped by adding 25 $\mu$l of 4M sulfuric acid to each well. Specifically-bound antibodies were detected by measuring the absorbance at OD 490 on an ELISA scanner C model EL310, Biotek Instruments Winooski, Vt.) within 30 min. Reactivity was graded as follows: $A_{490} \leq 0.15$, -; $A_{490} = 0.15$ to 0.3, 1+; $A_{490} = 0.3$ to 0.6, 2+; $A_{490} = 0.6$ to 1.2, 3+; $A_{490} \geq 1.2$, 4+. Hybridomas that were reactive with the immunizing FG cells but not with the lymphoblastoid 721-P cells were further screened for reactivity with frozen sections of HPC according to the procedure of Example II below. Only those that were reactive with frozen sections of HPC but not reactive with frozen sections of normal human liver, kidney and lung were selected. The two hybridoma cells lines selected for further study were designated HB 9318 and HB 9319, respectively.

III. CHARACTERIZATON OF MONOCLONAL REACTIVITY

EXAMPLE 2

A. REACTIVITY WITH HUMAN TUMOR TISSUES.

The reactivity of the monoclonal antibodies was determined by indirect immunoperoxidase staining as follows. Two- to 4-μm sections of frozen tissue blocks were cut on a cryotome, mounted on gelatin-coated glass slides, air-dried, and tested immediately in an indirect immunoperoxidase assay using the method of Taylor, *Arch. Pathol. Lab. Med.* 102:113 (1970). Briefly, after washing once in Hanks' balanced salt solution (Gibco, Grand Island, N.Y.) and phosphate buffered saline (PBS 10 mM sodium phosphate, 0.15M Nacl, pH 7.0), sections were incubated at room temperature sequentially with: diluting buffer (PBS containing 5% normal goat serum and 1% bovine serum albumin) for 15 min; a 1:2 dilution of hybridoma supernatants or appropriate isotype-matched controls for one hour; horseradish peroxidase-conjugated goat anti-mouse Ig antiserum (Bio-Rad, Richmond, Calif.) diluted 1:50 and containing 5% normal human serum for one hour; and finally substrate buffer (10 mM Tris, pH 7.4, 0.6 mg/ml 3,3'-diaminobenzidine, 0.015% $H_2O_2$) for 15 min. Washes with HBSS and PBS were performed between incubations. Sections were counterstained in 1% methylene blue, dehydrated through graded ethanol, washed in Histo-Clear (National Diagnostics, Somerville, N.J.), mounted in Pro-Texx (Lerner Laboratories, New Haven, Conn.), and examined by light microscopy.

Table 1 summarizes the reactivity of monoclonal antibodies produced by hybridoma cell lines HB 9318 and HB 9319 with 65 different tumors. HB 9318 was generally reactive only with carcinomas of the pancreas gastrointestinal tract, genitourinary tract, and head and neck tumors. Moreover, in virtually all instances, staining by the HB 9318 Mabs was distinctly associated with the basement membranes surrounding tumor foci, producing a characteristic one-sided basal surface staining of cells at the epithelial stromal interface. In the few cases of lung carcinomas, melanoma and breast cancer tissues that were stained, reactivity was also confined to the basement membranes.

Mab HB 9319 reacted with each of the seven pancreatic adenocarcinomas tested, including pancreatic carcinoma of the acinar cell type. Mab HB 9319 displayed a wide range of reactivity among tumor tissues examined. Moreover, reactivity of HB 9319 was generally intense with the majority of tumor cells within a tissue. Tumor cell basement membranes were also stained in some cases.

TABLE 1

REACTIVITY[a] OF MONOCLONAL ANTIBODIES WITH FRESH FROZEN HUMAN TUMOR TISSUE SECTIONS BY IMMUNOPEROXIDASE STAINING

|  | HB 9318 | HB 9319 |
|---|---|---|
| Pancreatic Cancer | | |
| ductal adenocarcinoma | −[b] | 2+ |
|  | 2+[b] | 1+ |
|  | 2+[b] | 4+ |
|  | − | 1 |
|  | 4+[b] | 1+ |
|  | 3+[b] | 3+ |
|  | 4+ | 4+ |
| islet cell Cancer/insulinoma | − | − |
| acinar cell Cancer | − | 1+ |
|  | − | 3+ |
| Oral Squamous Cancer | 1[b] | 3+ |
|  | 1[b] | 4+ |
|  | − | 2+ |
|  | −[b] | 4+ |
| Adenoid Cystic Cancer | 3+ | 2+ |
| Salivary Gland Cancer | 4+[b] | 3+ |
| Esophageal Cancer | 3+[b] | 3+ |
| Gastric Cancer | 3+[b] | 3+ |
|  | 2+ | 4+ |
|  | 3+ | 3+ |
|  | 1+[b] | 3+ |
| Colon Cancer | 3+[b] | 3+ |
|  | −[b] | 1+ |
|  | 3+ | 3+ |
|  | 3+[b] | 4+ |
| Hepatoma | − | 2+ |
|  | − | 2+ |
| Laryngeal Cancer | 2+[b] | 4+ |
|  | 2+[b] | 3+[b] |
| Melanoma | 1+[b] | 4+ |
|  | − | 4+ |
|  | − | 4+ |
| Sarcoma | − | 4+ |
|  | − | 4+ |
| Lung Cancer | | |
| adenocarcinoma | 1+ | 1+ |
|  | − | 3+ |
|  | − | 1+ |
| squamous Cancer | 1+[b] | 3+ |
|  | − | 2+ |
|  | − | 3+ |
|  | − | 3+ |
|  | − | 3+ |
| adenosquamous | 1+[b] | 3+ |
| oat cell Cancer | − | − |
|  | − | − |
| large cell Cancer | 4+ | 4+ |
| mesothelioma | − | 1+ |
| Breast Cancer | − | 3+ |
|  | − | 4+ |
|  | − | 3+ |
|  | − | 2+ |
|  | 1+ | 2+ |
| Cervical Cancer | 2+[b] | 1+ |
|  | 1+ | 4+ |
| Endometrial Cancer | − | 3+ |
|  | − | 4+ |
|  | 3+[b] | 2+ |
| Ovarian Cancer | − | 4+ |
|  | − | 3+ |
|  | 3+[b] | 2+ |
| Prostatic Cancer | 1+[b] | 4+ |
| Bladder Cancer | 1+[b] | 2+ |
|  | 3+[b] | 2+[b] |
| Kidney Cancer | − | 4+ |
|  | 2+ | − |

[a]Intensity of staining was scored from 1+ to 4+ with 4+ indicating greatest intensity and with "−" indicating lack of staining.
[b]Basement membrane staining.

B. REACTIVITY WITH HUMAN CELL LINES

The reactivity of Mabs against a panel of cell lines in culture was determined by ELISA reactivity, according to the Method of Schultz (1984), *Cancer Res.* 44:5914, as detailed in Example 1

Cells dried onto the bottom of 96-well miniplates were used as targets for ELISA. Horseradish peroxidase-conjugated goat anti-mouse Ig antiserum (BioRad, Richmond, Calif.) was used as the secondary antibody.

The reactivity of Mabs HB 9318 and HB 9319 is shown in Table 2. Both Mabs were reactive with the majority of the ten HPC cell lines tested. Moreover, both displayed particularly strong reactivity with cell lines derived from lung cancer, skin cancer and gastrointestinal and genitourinary tract tumors. HB 9319 displayed moderate to strong positivity with tumor cell lines of neuroectodermal origin including melanoma, glioblastoma and neuroblastoma lines. Both antibodies were generally non-reactive with human red blood cells of blood types AB+, A+, B+, O+, and O−, normal diploid fibroblasts and leukemic or lymphold cell lines.

TABLE 2
ELISA REACTIVITY OF MONOCLONAL ANTIBODIES WITH CULTURED HUMAN CELLS

| Cell lines (ATCC NO.) | HB 9318 | HB 9319 |
|---|---|---|
| Pancreatic Cancer | | |
| Colo 357[a] | 3+ | 2+ |
| FG[a] | 3+ | 3+ |
| SG[a] | 3+ | 3+ |
| FG-Met-2[a] | 4+ | 4+ |
| RWP-1[a] | 4+ | 2+ |
| RWP-2[a] | 3+ | 1+ |
| PANC-1 (CRL 1469) | 3+ | 3+ |
| ASPC-1 (CRL 1682) | 3+ | 1+ |
| Hs 766T (HTB 134) | 4+ | 1+ |
| BxPC-3 (CRL 1687) | 4+ | 4+ |
| Lung Cancer | | |
| adenocarcinoma | | |
| UCLA-P3[b] | − | 2+ |
| A549 (CCL 185) | 2+ | 1+ |
| CALU 6 (HTB 56) | − | 4+ |
| squamous cancer | | |
| T-222[b] | 2+ | 4+ |
| SK-MES-1 (HTB 58) | 3+ | 3+ |
| CALU-1 (HTB 54) | 2+ | 3+ |
| USCLS-1[b] | 3+ | 3+ |
| oat cell Cancer | | |
| T-293[c] | − | 1+ |
| NCI-H69 (HTB 119) | − | − |
| Breast Cancer | | |
| 734B[d] | − | 3+ |
| BT-20 (HTB 19) | 3+ | 4+ |
| MDA-MB-435S (HTB 129) | − | 3+ |
| Bladder Cancer | | |
| T24 (HTB 4) | − | 2+ |
| J82 (HTB 1) | − | 2+ |
| 5637 (HTB 9) | 2+ | 3+ |
| Cervical Cancer | | |
| ME-180 (HTB 33) | 3+ | 4+ |
| Prostatic Cancer | | |
| DU-145 (HTB 43) | 2+ | 3+ |
| Pharyngeal Cancer | | |
| FaDu (HTB 43) | 3+ | 4+ |
| Skin cancer | | |
| A-431 (CRL 1555) | 3+ | 3+ |
| Colon Cancer | | |
| COLO 396[d] | 4+ | 4+ |
| Hepatoma | | |
| SK-HEP-1 (HTB 52) | 3+ | 2+ |
| Mesodermal Tumor | | |
| SK-UT 1 (HTB 114) | − | 2+ |
| Melanoma | | |
| ML-873-1[c] | − | 2+ |
| WM239A[c] | − | 3+ |
| WM2664 (CRL 1676) | − | 3+ |
| A375P[c] | − | 4+ |
| A-375M[c] | − | 3+ |
| M14[c] | − | 3+ |
| M21[c] | − | 4+ |
| MS-1[c] | − | 3+ |
| FOSS[c] | − | 3+ |
| Melur[c] | − | 3+ |
| Glioblastoma | | |
| U38MG (HTB 16) | − | 1+ |
| U87MG (HTB 14) | − | 3+ |
| U-373MG (HTB 17) | − | 3+ |
| Neuroblastoma | | |
| SK-N-SH (HTB 11) | − | 2+ |
| SK-N-MC (HTB 10) | − | − |
| LAN-1[c] | 2+ | 1+ |
| B-Lymphoblastoid | | |
| L14[b] | − | 1+ |
| LG-2[b] | − | 1+ |
| 721-P[e] | − | − |
| GM3107[b] | − | 2+ |
| T-Lymphoblastoid | | |
| MOLT-4 (CRL 1582) | − | − |
| HPB-ALL[b] | − | 2+ |
| HSB-2[d] | − | − |
| Promyelocytic Leukemia | | |
| HL-60 (CCL 240) | − | − |
| Erythroleukemia | | |
| K562 (CCL 243) | − | − |
| Diploid Fibroblast | | |
| WI-38 (CCL 75) | − | − |
| Human RBC | − | − |

Cell lines were obtained as follows:
[a]P. Meitner, Department of Medicine, Brown University
[b]L. Walker, Department of Immunology, Scripps Clinic and Research Foundation
[c]R. Reisfeld, Department of Immunology, Scripps Clinic and Research Foundation
[d]T. Edginton, Department of Immunology, Scripps Clinic and Research Foundation
[e]F. Bach, University of Minnesota.

C. REACTIVITY WITH NON-MALIGNANT PATHOLOGIC HUMAN TISSUES

The reactivity of the Mabs with a panel of inflammatory pancreases, benign tumor and hyperplastic epithelia was determined by indirect immunoperoxidase staining of frozen tissue sections, according to the method of section A, above. Both Mab HB 9318 and Mab HB 9319 showed some reactivity with the duct cells of chronic pancreatitis tissues. Mab HB 9319 was widely reactive in that it stained every non-malignant pathologic tissue examined, although always in discrete areas. Table 3 shows the results of testing with this panel of tissues.

TABLE 3
REACTIVITY OF MONOCLONAL ANTIBODIES WITH FRESH FROZEN NON-MALIGNANT PATHOLOGIC HUMAN TISSUE SECTIONS BY IMMUNOPEROXIDASE STAINING

| | HB 9318 | | HB 9319 | |
|---|---|---|---|---|
| Pancreas (chronic pancreatitis) | | | | |
| acini | − | − | − | − |
| ducts | 2+ | −[b] | 2+ | 1+ |
| islets of Langerhans | − | − | − | − |
| Pancreas (SLE)[a] | | | | |
| acini | − | | 4+ | |
| ducts | −[b] | | − | |
| islets of Langerhans | − | | − | |
| Uterus (leiomyoma) | − | − | 3+ 4+ | 4+ 4+ |
| Ovary (fibroadenoma) | − | | 2+ | |
| Endometrium (hyperplastic) | 3+ | | 4+ | |
| Prostate (hyperplastic) | | | | |
| upper layers of epithelium | − | | 3+ | |
| basal layers of epithelium | 4+ | | 3+ | |
| basement membrane | 4+ | | − | |

D. REACTIVITY WITH NORMAL ADULT AND FETAL TISSUES.

The reactivity of the Mabs with fresh frozen normal adult and fetal tissues was determined by indirect immunoperoxidase staining according to the method of section A, above. The antibodies were unreactive with the vast majority of normal tissues examined.

Mab HB 9318 displayed some reactivity with the basal epithelial layers or basement membranes of the esophagus, cervix, and large intestine, plantar skin, breast tissue and ileal epithelium. The restricted expression of the HB 9318 antigen by the proliferating cell layers of normal stratified epithelia and its localization at the epithelial stromal interface suggests that this molecule may be an early differentiation antigen (possibly involved in cell adhesion) of epithelial cells that is re-expressed following malignant transformation. Further, the HB 9318 antigen may be useful for diagnosis and therapeutic intervention of other skin-related disorders such as psoriasis and basal cell carcinomas and may prove to be a valuable cell surface marker for investigating epidermal cell biology.

Mab HB 9319 reacted with the acinar cells of adult and fetal pancreases, fetal pancreatic ducts, and the parenchyma and bile ducts of ⅓ livers that were tested. It was moderately reactive with the esophagus, stomach and small intestine, cervix, uterus, breast, fetal and adult lung parenchyma, fetal kidney, cerebral cortex, and with the molecular layers and Purkinje cells within the adult cerebellum. All layers of plantar skin including basement membrane were also intensely stained.

Table 4 summarizes the results of this panel of tests.

TABLE 4

REACTIVITY OF MONOCLONAL ANTIBODIES WITH FRESH FROZEN NORMAL HUMAN TISSUE SECTIONS BY IMMUNOPEROXIDASE STAINING

|  | HB 9318 | HB 9319 |
|---|---|---|
| Esophagus | | |
| stratified squamous epithelium | | |
| upper layers | — | 3+ |
| basal layers | 4+ | 4+ |
| basement membrane | 4+ | — |
| Stomach | | |
| gastric pits | — | 3+ |
| gastric glands | | |
| parietal cells | — | 2+ |
| chief cells | — | 2+ |
| lamina propria | — | 1+ |
| Small Intestine | | |
| jejunal epithelium | — | 2+ |
| ileal epithelium | 3+ | 3+ |
| basement membrane | 4+ | — |
| Large Intestine | | |
| colonic epithelium | — | 1+ |
| crypts of Lieberkuhn | — | 1+ |
| basement membrane | 4+ | — |
| lamina propria | — | 1+ |
| Liver | | |
| parenchyma | — — — | — 3+ — |
| bile ducts | — 1+ — | — 3+ — |
| Pancreas (adult) | | |
| acini | — — — — | 4+ 4+ 4+ 4+ |
| ducts | — — —ᵃ — | — — — — |
| islets of Langerhans | — — — — | — — — — |
| Pancreas (fetal) | | |
| acini | — | 4+ |
| ducts | —ᵃ | 4+ |
| islets of Langerhans | — | — |
| Thymus | | |
| cortex | — | — |
| medulla | — | — |

TABLE 4-continued

REACTIVITY OF MONOCLONAL ANTIBODIES WITH FRESH FROZEN NORMAL HUMAN TISSUE SECTIONS BY IMMUNOPEROXIDASE STAINING

|  | HB 9318 | HB 9319 |
|---|---|---|
| Lymph node | | |
| nodules | — | — |
| germinal centers | — | 1+ |
| Spleen | | |
| white pulp | — | — |
| red pulp | — | 1+ 1+ |
| Kidney (adult) | | |
| glomeruli | — — — | — — — |
| proximal tubules | — — — | — — — |
| distal tubules | — — — | — — — |
| Kidney (fetal) | | |
| glomeruli | — | 3+ |
| proximal tubules | 1+ | 3+ |
| distal tubules | — | 3+ |
| Cervix | | |
| columnar epithelium | — 1+ | 4+ 3+ |
| basement membrane | 4+ 4+ | — — |
| squamous epithelium | | |
| upper layers | — — | 3+ 3+ |
| basal layers | 4+ 4+ | 4+ 4+ |
| basement membrane | 4+ 4+ | — — |
| Uterus | | |
| endometrium | 1+ — | 3+ 2+ |
| myometrium | — — | 4+ 2+ |
| Ovary | | |
| cortex | — | — |
| medulla | — | — |
| Breast | | |
| lobule | 4+ 2+ | 4+ 4+ |
| duct | 4+ 3+ | 4+ 4+ |
| basement membrane | 4+ 4+ | 4+ 4+ |
| Lung (adult) | | |
| parenchyma | — — — | 2+ 2+ — |
| Lung (fetal) | | |
| parenchyma | — | 3+ |
| Thyroid | | |
| epithelial cells | — | 1+ |
| colloid | — | — |
| Cerebrum | | |
| cortex | — | 3+ |
| Cerebellum | | |
| granular layer | — | — |
| molecular layer | — | 2+ |
| Purkinje cells | — | 2+ |
| Plantar skin | | |
| stratum corneum | — | 3+ |
| stratum granulosum | — | 3+ |
| stratum spinosum | 1+ | 3+ |
| stratum germinativum | 3+ | 4+ |
| basement membrane | 4+ | 4+ |

ᵃBasement membrane staining

E. REACTIVITY WITH CELL SURFACES

To determine whether the antigens recognized by the Mabs were expressed on surface of cells of reactive tissues, viable HPC cells were tested with the Mabs in indirect immunofluorescence assays as follows:

INDIRECT IMMUNOFLUORESCENCE STAINING

Cells grown to confluence on glass cover slips were washed once with cold HBSS, overlaid with 0.1 ml of 1:2 hybridoma supernatant for one hour at 4° C., washed in cold HBSS, and overlaid with 0.1 ml of 1:50 fluorescein isothiocyanate-conjugated goat anti-mouse Ig antiserum (Tago, Burlingame, Calif.) for one hour at 4° C. After washing and fixing in 3% paraformaldehyde, cells were mounted in 80% glycerol, 1 mg/ml p-phenylenediamine, 200 mM Tris, pH 8.5, examined and photographed with a Zeiss fluorescence microscope.

Both Mab HB 9318 and HB 9319 showed distinct staining of the plasma membrane, indicating recognition of cell surface structures. Both stained the entire cell population, displaying a contiguous, linear membrane pattern.

IV. ANTIGEN CHARACTERIZATION

EXAMPLE 3

IMMUNOCHEMICAL CHARACTERIZATION OF ANTIGENS

In order to assess the chemical nature of the antigens recognized by Mabs, HPC cells were radiolabeled by incubation with either L-[$^3$H] leucine or [$^3$H] glucosamine, detergent solubilized and then subjected to immunoprecipitation with Mab immunosorbents, as follows:

Ten $\mu$l of a 10% suspension of protein-A-Sepharose (Pharmacia, Uppsala, Sweden) were incubated at 4° C. for 1 hour with 5 $\mu$l of rabbit anti-mouse Ig antibodies (Accurate Chemicals, Westbury, N.Y.) in 0.3 ml of PORT buffer (10 mM Tris, pH 8.5, 0.15M NaCl, 0.5% Tween 20, 0.1% Renex 30, 2.5 mM sodium azide, 0.1% ovalbumin). After washing twice with PORT buffer, incubating 1 hour at 4° C. with 1 ml hybridoma supernatants and washing twice with PORT buffer, the beads were incubated overnight at 4° C. with radiolabeled cell extract ((1–2×10$^7$ cpm). The immunosorbents were washed 8 times with PORT buffer (10 mM Tris, pH 8.5, 0.15M NaCl, 0.5% Tween 20, 0.1% Renex 30, 2.5 mM sodium azide) and bound antigens were eluted in Laemmli buffer (Nature 227:680(1970)). The samples were analyzed by SDS-PAGE on slab gels and visualized by fluorography.

Initial results of the SDS-PAGE analysis indicated that Mab HB 9318 recognized a doublet protein antigen, of 205 kd and 135 kd, respectively. Both bands were glycosylated as they incorporated [$^3$H]-glucosamine. In some cases two additional bands of 150 kd and 185 kd were also seen. A band of 116 kd co-precipitated with HB 9318 bands, but was non-specific since it could be removed by preabsorption with control immunosorbants. Mab HB 9319 recognized a highly glycosylated 140 kd protein.

Immunoprecipitation of a metabolically labeled HPC indicated that the antigenic determinants recognized by each of the monoclonals are carried by protein molecules. These proteins are also glycosylated, so that it remains to be determined whether the recognized epitopes are expressed by the protein or the glycan part of these molecules.

EXAMPLE 4

CHARACTERISTICS OF HB 9318 ANTIGEN

Characterization of the antigen which immunoprecipitates with HB 9318 demonstrates that it is a two-chain heterodimer which is a member of the integrin class of cell adhesion receptors.

Integrins are heterodimers comprised of noncovalently associated transmembrane glycoproteins. (reviews of the characteristics of integrins have been published by Hynes, R. O., *Cell* (1987) 48:549–554; Ruoslahti, E., et al, *Science* (1987) 238:491–497; and Buck, C. A. & Horwitz, A. F. (1987) *Ann. Rev. Cell. Biol.* 3:179–205. The $\alpha$-chains have high degrees of homology and the differences in the $\beta$-chain serve to place the various integrins into subfamilies. Integrin heterodimers are grouped into three families, based on which of the three $\beta$-chains ($\beta_1$, $\beta_2$ or $\beta_3$) they contain. The integrin of the present invention is believed to represent a fourth member of the integrin family because of its structurally distinct $\beta$-chain.

The integrin class of cell surface adhesion receptors is distinct from another type designated CAMs which are monomers which use polysialylation as a control element. The integrin to which HB 9318 binds is distinguished from other known integrins by its polysialylation. The designation of $\alpha_E\beta_4$ has been proposed as a designation for this novel integrin. Alternatively, the name intepsin has been proposed for this antigen.

The HB 9318 antigen contains two non-covalently bound glycopeptides, designated herein gp205 and gp125. The gp125 represents an analog to the $\alpha$-chains of other integrins, the gp205 peptide is analogous to other integrin $\beta$-chains, and has been shown to be polysialylated. This two-chain antigen has been shown by immunoperoxidase staining to be expressed only on the basolateral surfaces of the germinative layer of epithelial cells while cells from the prickle-cell layer outwards were progressively devoid of reactivity. The integrin is evidently involved in cell adhesion.

When HB 9318 monoclonal antibody is used to immunoprecipitate pancreatic cancer cell lysates gp125 and gp205 are precipitated. When HB 9318 monoclonal antibody is used to immunoprecipitate placental cell lysates, gp125 is again precipitated, however a second gp150 $\beta$ subunit is precipitated. This gp150 appears to be identical to the gp205 $\beta$ subunit present in pancreatic cancer, with the exception that it is not as glycosylated.

A. DISTRIBUTION OF THE ANTIGEN AND $\alpha$- AND $\beta$-CHAINS

Immunohistology of human epidermal sections with HB 9318 shows that staining is concentrated near the basement membrane and basolateral cell surfaces of the germinative layer. Upper cell layers are progressively devoid of reactivity. Thus its expression is restricted to this particular portion of the cell surface.

FG-met2 pancreatic carcinoma cells were used as test substrates; lung adenocarcinoma lines and short term normal human keratinocyte cultures gave identical results.

Cultures of FG-met2 pancreatic carcinoma cells were surface radioiodinated using $^{125}$-I sodium iodide in standard protocols. Detergent lysates of these labeled cells were immunoprecipitated with HB 9318, and the immunoprecipitate applied to polyacrylamide gels under reducing and non-reducing conditions. Under reducing conditions, a 205 kd band was detected; under non-reducing conditions the single band appeared at 190 kd. This represents the $\beta$-chain of intepsin, designated herein gp205.

The $\alpha$-chain, which migrates as a 150 kd band under non-reducing conditions, and a 125 kd band under reducing conditions was detectable only when the cells were metabolically labeled either with [$^{35}$S]-methionine or with tritiated glucosamine. It is believed that the absence of the 125 kd/150 kd bands from the surface-labeled cells is due to an artifact of the iodination procedure.

That gp205 and gp125 components are non-covalently associated with each other at the cell surface was verified by treating FG-met2 cells (a human pancreatic carcinoma line) with a membrane impermeable cross-linker, DTSSP, and lysing the cells with detergent. This resulted in a 400 kd band upon SDS-PAGE. The 400 kd band disappeared and was replaced by 205 kd and 125 kd by subjecting the preparation to reduction, as DTSSP results in reversible cross-linking. The non-covalent complexing of gp205 and gp125 was further confirmed by immunoprecipitating protein from FG-met2 which had been labeled with [$^{35}$S]-methionine. The immunoprecipitate showed an approximate MW of 500 kd as analyzed by gel filtration. (The discrepancy in apparent MW is an artifact of the procedures.)

B. PURIFICATION OF qp205 AND qp125

The surface proteins were isolated both from the lung adenocarcinoma cell line UCLA-P3 and from FG-met2.

The cells were grown in sufficient quantity to obtain 50 g wet weight and 20 g wet weight respectively. After washing, the cells were lysed in an equal volume of TBS containing 2% Renex 30, centrifuged at 10,000 ×g for 30 min at 4° C. and stored at −70° C.

The lysates were passed sequentially through a Sepharose column and through one or two sequential HB 9318 immunosorbent columns at 5–10 ml/hr. After washing with TBS containing 0.1% Renex 30, pH 8.5 to remove unadsorbed material, the HB 9318 column was inverted, washed with 3 column volumes of TBS, pH 8.5 containing 1.0% n-octyl β-D-glucopyranoside, and the bound material eluted with 50 mM diethylamine, pH 11.5 containing 150 mMNaCl, 1.0% n-octyl β-D-glucopyranoside. Eluted material was collected in 1.5 ml Eppendorf tubes containing 0.1M Tris HCl pH 6.8, 150 mM NaCl, and 1.0% n-octyl β-D-glucopyranoside, to lower the pH rapidly to approximately 8.5. Elution was detected by SDS-PAGE stained with silver stain or Coomassie blue, and eluate from peaks containing protein was pooled and concentrated.

C. AMINO ACID SEQUENCING OF PURIFIED ANTIGEN

Figure 4:
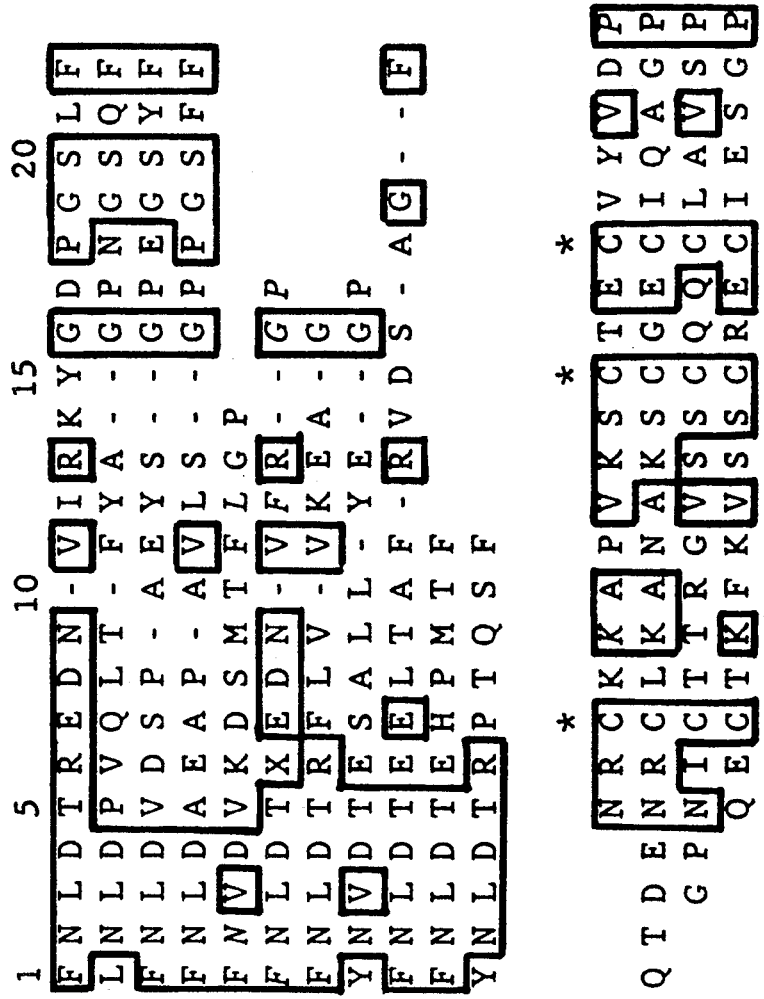
FIG. 4 shows a comparison of N-terminal sequences of various integrin α- and β-chains.

Antigen corresponding to gp205 and to gp125, purified as above was subjected to amino acid sequencing from the N-termini using standard techniques. The gp125 fragment had the N-terminal sequence:

F-N-L-D-T-R-E-D-N-V-I-R-K-Y-G-D-P-G-S-L-F which shows extensive homology with α N-terminal sequences of α-chains in other integrins, as illustrated in FIG. 4.

The gp150 fragment had the N-terminal sequence:

N-R-C-K-K-A-P-V-K-S-C-T-E-C-V-Y-V-D-P which shows extensive homology with β N-terminal P47 sequences of β-chains in other integrins, as illustrated in FIG. 4.

Figure 3A:
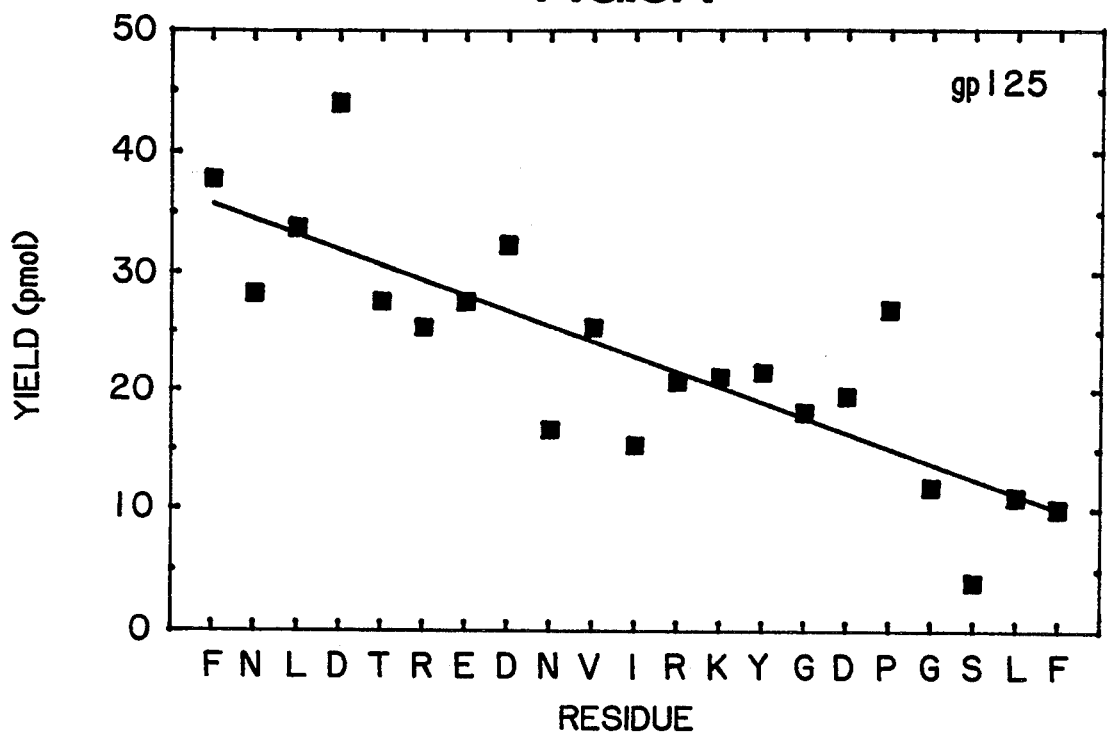
FIGS. 3A and 3B show amino acid residue sequences of α-chain, gp125 and β-chain, gp150 purified using HB 9318.
Figure 3B:
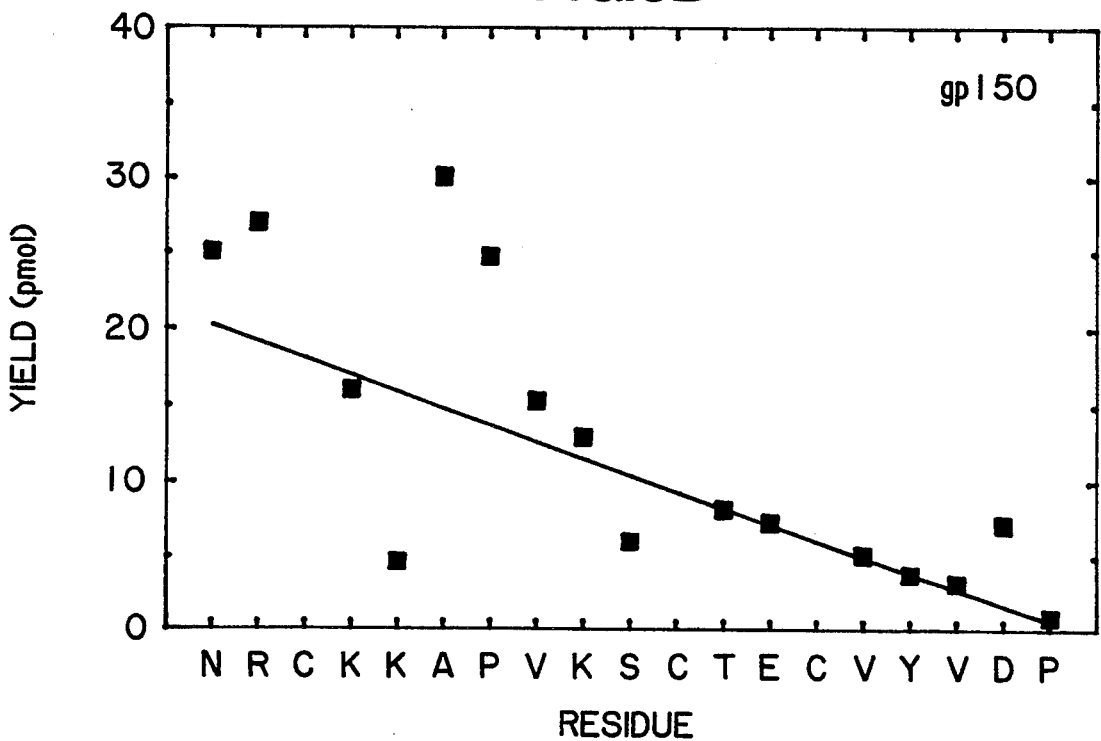

In addition, FIGS. 3A and 3B show the amino acid residue sequences of the gp125 α-chain and the gp150 as precipitated by the HB 9318 antibody.

The gp205 β-chain is apparently blocked at the N-terminus.

Automated microsequencing of gp125, purified on an HB 9318 immunoaffinity column from either carcinoma cells or placental tissues yielded information up to residue 21. The sequences of gp125 from these two sources were identical, with the exception of position 6 which could not be assigned for carcinoma gp125 in three separate sequencing runs. The gp125 sequence showed several similarities with integrin α chain N-termini, as depicted in FIG. 4. The first five residues, FNLDT, are identical in four α chains, and occur with one replacement in four other α chains and with two replacements in the remaining three α chains. Another segment of significant homology among α chains occurs between residues 15 and 21. In this region, gp125 shares one residue with at least one other α chain at five positions, and at three positions has unique residues. Overall, the homology of gp125 to the integrin α chains appears to be equivalent to the homology of the α chains to each other. The highest level of similarity was observed with the VLA-2 α chain, where eleven of thirteen residues available for comparison are shared.

Placenta gp150 was sequenced up to residue 19 (FIG. 3B). When this sequence was compared to the amino-termini of the three human integrin β chains, several similarities were found (FIG. 4). Of particular importance is the exact correspondence of the three cysteines, the serine in position 10 and the proline in position 19, as these residues are invariant among integrin β chains. Overall, gp150 showed eleven identities with $β_1$, eight with $β_2$ and seven with $β_3$. However, the gp150 sequence was distinct from those of the other β chains since its N-terminus was offset with respect to $β_1$ (as predicted from cDNAs) and $β_3$ sequences, and since it contained six unique residues (FIG. 4).

To further check the relationship between gp150 and gp180, placental gp180 was also sequenced up to residue 13. This sequence was identical to gp150 (not shown), except for four residues of uncertain assignment, thus providing further evidence for the structural similarity of gp150 and gp180. Since the neuraminidase digestions suggested that the $M_r$ differences between gp205, gp180 and gp150 are due to variations in sialic acid content, gp205 was expected to display an amino-terminal sequence identical to that of gp150 and gp180. However, gp205 is undetectable in placental lysates, and two attempts to sequence carcinoma-derived gp205 failed, presumably due to insufficient quantities and/or N-blocking during purification.

D. METABOLIC LABELING WITH [$^{35}$S]-METHIONINE IN THE PRESENCE OF TUNICAMYCIN

Indirect immunoprecipitation with Mab HB 9318 of detergent lysates of cells intrinsically labeled with [$^{35}$S]-methionine in the presence of tunicamycin (an inhibitor of N-linked glycosylation) and subsequent analysis by SDS-PAGE under reducing conditions revealed the presence of two major bands of 190 kd and 100 kd, respectively.

Semiconfluent cultures of FG cells were incubated for 10–12 hours at 37° C. with 1 μg/ml tunicamycin. The cells were then pulsed for an additional 12 hours with 1 mCi [$^{35}$S]-methionine in methionine-free RPMI medium containing 3% FCS and 1 μg/ml tunicamycin. Control flasks, similarly labeled with [$^{35}$S]-methionine in the absence of tunicaymcin, were also prepared. The metabolically-labeled cells were then harvested as previously described and lysed using RIPA lysis buffer. Cell lysates were clarified by centrifugation at 100,000 ×g for 45 min at 4° C. and subsequent storage was at −70° C.

E. TWO-DIMENSIONAL GEL ANALYSES

Immunoprecipitations were carried out by overnight incubation of cell lysates with immunoabsorbents prepared by activated-CNBr conjugation of Mab to Sepharose 4B-CL beads (Pharmacia, Uppsala, Sweden). After elution in 8M urea at room temperature, samples were analyzed by two-dimensional electrophoresis, consisting of nonequilibrium pH electrophoresis on tube gels in the first dimension, followed by SDS-PAGE on 7.5 % acrylamide slab gels. Gels were impregnated with 2, 5,-diphenyloxazole, dried and exposed for the indicated times to Kodak XAR-5 X-ray film at −70° C. The resulting pattern of migration is shown in FIG. 1.

F. CHARACTERIZATION OF THE qp205 AS A POLYSIALYLATE INTEGRIN β-CHAIN

Both gp205 and gp125, alone or together were treated with various enzymes which cleave carbohydrate chains.

EndoF and EndoH cleave N-linked complex oligosaccharides, and the results were consistent with one or two such oligosaccharides on gp205 and three or four on gp125:

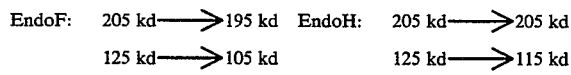

Neuraminidase (NA) cleaves complex N-linked carbohydrates and polysialyl chains; endo-N-acetyl-neuraminidase (Endo-N) cleaves polysialylates only as α-2,8-linked linear sialic acid homopolymers. The results were consistent with gp205 as a polysialylated integrin β-chain:

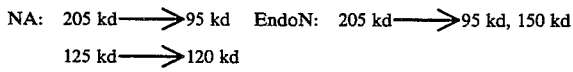

These results are consistent with a heavily polysialylated β integrin chain wherein the sialylation is through β-linkage. (Most integrin β-chains have MW of 95–125 kd).

G. BINDING TO LECTINS

When radiolabeled lysates were preabsorbed with lentil lectin-agarose beads (Vector Labs, Burlingame, Calif.), the antigens reactive with HB 9318 were removed. Removal of antigen was shown by immunoprecipitation of bead supernatant, followed by SDS-PAGE. Similar treatment of radiolabeled lysates with wheat germ agglutinin-agarose beads (E.Y. Labs., San Mateo, Calif.) did not remove the HB 9318 antigen. Therefore, the antigen reactive with HB 9318 was characteristically bound to lentil lectin, but not to wheat germ agglutinin.

H. GEL FILTRATON OF ANTIGEN

Radiolabeled detergent cell lysates were absorbed on wheat germ agglutinin-Sepharose columns (E.Y. Labs, San Meteo, Calif.), The breakthrough was absorbed onto lentil lectin-Sepharose columns. After washing, the absorbed material was eluted by the addition of 2% alpha-methyl-mannoside (Sigma Chemical Co., St. Louis). The eluted material was subjected to gel filtration, in the presence of 10 mM Tris, pH 8.0 containing 0.15M NaCl, 1 mM $CaCl_2$, mM $MgCl_2.6H_2O$, 0.02% sodium azide and 0.1% Renex 30 by using an FPLC instrument (Pharmacia, Uppsala, Sweden), equipped with a Sepharose 6 column. Molecular weight standards were run in parallel. One ml fractions were collected (approximately 40 fractions), and subjected to immunoprecipitation with HB 9318 antibody. SDS-PAGE analysis of immunoprecipitates revealed that the following molecular species were reactive with HB 9318 in the indicated fractions:

| SDS-PAGE m.w. | Fraction # | FPLC MW |
|---|---|---|
| 135; 205 | 25 | 669 kd |
| 135; 205 | 26 | 669 kd |
| 135; 150; 205 | 27 | approximately 669 kd |
| 135; 150; 205 | 28 | approximately 669 kd |
| 135; 150; 205 | 29 | between 669 kd and 440 kd |
| 135; 150 | 30 | between 669 kd and 440 kd |
| 135; only | 31–36 | between 440 kd and 232 kd |

The estimated molecular weights corresponding to the FPLC fractions are indicated in the right column. Since the estimated MW exceeds the MW determined by SDS-PAGE, the HB 9318 antigens must exist as multimeric complexes, probably heterodimers formed by the association of one 205 kd component with one 125 kd component. The presence of excess free 125 kd component was also suggested by the material immunoprecipitated from fractions 31–36.

I. PULSE CHASE BIOSYNTHETIC STUDIES:

Single cell suspensions of exponentially growing FG cells were propagated for one hour at 37° C. in methionine-free medium (Irvine Scientific, Santa Ana, Calif.) and then pulse labeled for 10 min with [$^{35}$S]methionine (1295 Ci/mM NEN Research Products, Boston, Mass.) at a concentration of 1.0–1.5 mCi/$3 \times 10^7$ cells/mi. After the removal of an aliquot of $5 \times 10^6$ cells that constituted the zero-time point, the remaining cells were washed three times with cold Tris-buffer, pH 7.5 containing 10 mM unlabeled L-methionine (Sigma Chemical Co., St. Louis, Mo.). The labeled cells were resuspended in complete medium containing 10 mM unlabeled methionine and incubated on a shaker at 37° C. Aliquots were removed at the different time points indicated and the cells were centrifuged and extracted in RIPA lysis buffer as previously described.

After a 10 minute pulse with [$^{35}$S]-methionine, a faint band of 150 kd was detected at the zero time point of chase. This 150 kd component was clearly visible after 15 minutes of chase. Within the next 45 minutes of chase it appeared to be processed and the appearance of the 135 kd component was seen. Both the 205 kd and 135 kd molecules were detectable after 4 hours of chase until up to 20 hours of chase. It is presently not clear whether a precursor/product relationship exists between the two forms of the HB 9318 antigen. While not wishing to be bound by the explanation, it appears that post-translational processing of the 150 kd molecule gives rise to the 135 kd subunit. Moreover, the 205 kd component could either arise by further processing of 135 kd component or by altered processing of the 150 kd precursor. Alternatively, it could have its own precursor molecule that is not recognized by Mab HB 9318, thereby suggesting that the HB 9318 antigen is a heterodimer comprised of two distinct non-covalently linked subunits.

Western blots of material immunopurified with HB 9318 from carcinoma cells and placental tissue in which 5710 antiserum reacted predominantly with gp205, gp180, and gp150 and displayed little, if any, reactivity with gp125. This antigenic similarity of gp205, gp180, and gp150 was authentic since, in a further refinement, antibodies that were adsorbed and eluted from gp150 reacted with gp180 (in addition to gp150 itself). Antibodies adsorbed and eluted from gp180 reacted with gp150 (in addition to gp180 itself). Furthermore, $S$35-methionine labeled gp205, gp180, gp150 and gp125 purified by immunoaffinity and electroelution were subject to "hot" blotting with gp150 purified antibodies. These antibodies only reacted with gp205, gp180, and gp150, but not with gp125. Subsequent autoradiography of the blot confirmed that the four proteins were present in approximately equal amounts. These results provided further evidence for the structural relatedness for gp205, gp180, and gp150, and for the dissimilarity of gp125. Therefore, co-precipitation of gp125 by HB 9318 and 5710 antibodies is probably due to noncovalent associations with gp205, gp180 and gp150.

J. LIMITED PEPTIDE MAPPING

Limited peptide mapping was used to determine the structural relationships between gp205 and gp125. Cells labeled with [$^{35}$S]-methionine were immunoprecipitated with HB 9318 and subjected to SDS-PAGE. The bands to be analyzed were located on the dried gel by autoradiography. These bands were then excised from the gel, rehydrated and inserted in slots on a 15% acrylamide SDS-PAGE gel containing a 0.5 microgram/ml solution of *Staphylococcus aureus* V8 protease (Cleveland, et al. (1977) *J. Biol. Chem.* 252: 1102–1106.) After the bands were stacked, electrophoresis was suspended for 30 min. to allow enzymatic digestion. The gels were thereafter fluorographed.

SDS-PAGE resolved eight peptides for gp205 and ten peptides for gp125. Each generated distinct profiles, suggesting that gp205 and gp125 are structurally unrelated. HB 9318 precipitates two minor bands, gp180 and gp150. Limited peptide mapping of gp180 resolved seven fragments; gp150 resolved six fragments. The fragments of both gp180 and gp150 co-migrated with gp205 fragments, except for one gp150 peptide which co-migrated with the major fragment of gp125. (Due to its significantly greater intensity, this fragment may be derived from minor contamination of gp150 with the closely-spaced gp125.) These data suggest that gp205, gp180, and gp150 are structurally related, but distinct from gp125.

This conclusion was further supported by investigations with a polyclonal antiserum (5710) raised against antigen purified from carcinoma cells by immunoaffinity chromatography on the monoclonal antibody HB 9318. Antiserum 5710 was prepared by bleeding of an NZW rabbit, subcuraneously injected with approximately 2 micrograms of immunopurified carcinoma HB 9318 antigen at day 0 in Freund's complete adjuvant, and at days 30 and 45 with the same amount of antigen in incomplete adjuvant.

From carcinoma lysates, the 5710 antiserum precipitated a set of proteins identical to those reactive with HB 9318. If, however, the cell lysates were previously treated at 100° C. in the presence of SDS to disrupt noncovalent associations, then antiserum 5710 precipitated only gp205, gp180 and gp150, but not gp125. The isolated gp205, gp180 and gp150 displayed their characteristic $M_r$ downshift under nonreducing conditions. These results suggest that at least some of the epitopes present on gp205, gp180 and gp150 are not found on gp125 and that all 5710 epitopes on gp125, if any, are sensitive to denaturation. This conclusion was verified by Western and "hot" blots.

K. Western and "hot" Blots

The general procedure of Towbin, H. et al. (1979) *Proc. Nat'l. Acad. Sci. USA* 76:4350–4354, was followed. Proteins separated by SDS-PAGE on a 5% gel were transferred overnight at 4° C. to Immobiolon (Millipore Corp., Bedford Mass.) using a 25 mM Tris, 192 mM glycine buffer. The filter was saturated with 3% (w/v) nonfat dry milk in TBS, pH 8.0 with 0.05% Tween 20 and 0.02% azide, incubated for 3 h with primary antibody, washed, overlaid for 1 hour with alkaline phosphatase-conjugated goat anti-rabbit (Promega Biotec, Madison, Wis.) or anti-mouse (Boehringer Mannheim, Indianapolis, Ind.) IgG, washed again and then developed with 0.33 mg/ml 5-bromo-4-chloro-3-indolyl phosphate in 100 mM Tris-HCL pH 9.5, 100 mM NaCl, 5 mM MgCl$_2$, followed by 5 mM EDTA in 20 mM Tris-HCl pH 8.0. For affinity purification (Weinberger, C., et al. (1985) *Science* 228:740–742) of 5710 antibodies, vertical strips cut from the edges of gp205, gp125 whole-gel blots previously incubated with 5710 were developed to locate reactive bands. Horizontal strips corresponding to these were excised from the undeveloped mid-part of the filter. Bound antibodies were eluted by three one-minute washes with 5 mM glycine-HCl pH 2.3 containing 150 mM NaCl, 0.05% Tween 20, 100 micrograms/ml bovine serum albumin, 2.5 mM sodium azide, and quickly neutralized by addition of Tris-HCl pH 8.0.

For "hot" blots, 1×10$^7$ cells were metabolically labeled with [$^{35}$S]-methionine, immunoprecipitated with HB 9318 and electrophoresed on a 5% SDS-PAGE gel. The wet gel was autoradiographed overnight to locate radioactive bands, which were then excised. Proteins were electroeluted in an ISCO apparatus as described (Hunkapiller, M .W., et al (1983) *Methods Enzymol.* 91:399–413), run on a 5% SDS-PAGE and transferred to Immobilon filters. The filters were first immunostained and then autoradiographed.

EXAMPLE 5

ADDITIONAL BIOCHEMICAL CHARACTERISTICS OF HB 9319 ANTIGEN

A. MOLECULAR PROFILE UNDER NON-REDUCING CONDITIONS

FG-met2 cells labeled with [$^{35}$S]-methionine were immunoprecipitated using HB 9319 and analyzed by SDS-PAGE under non-reducing conditions. HB 9319 antigen migrates as a single band of 125 kd under these conditions.

B. EXTRINSIC RADIOLABELING WITH $^{125}$I

Cultures of FG-met2 cells were surface iodinated using $^{125}$-I sodium iodide, and detergent lysates were immunoprecipitated with HB 9319. The precipitated antigen migrates on SDS-PAGE under reducing conditions as a single species of 140 kd.

Similar results were obtained when the antigen was labeled metabolically with labeled inorganic sulfate or phosphate.

C. METABOLIC LABELING WITH [35S]-METHIONINE IN THE PRESENCE OF TUNICAMYCIN

The method follows that of Example 4(D) using HB 9319 in place of HB 9318. HB 9319 immunoprecipitated a single band in SDS-PAGE of 100 kd under reducing conditions.

D. TWO-DIMENSIONAL GEL ANALYSIS

Figure 2:
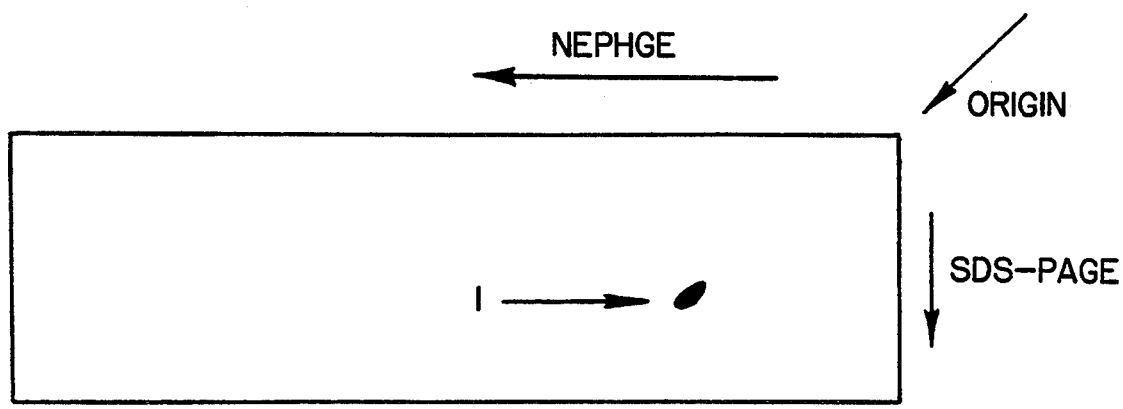
FIG. 2 shows two-dimension gel analysis of immunoprecipitates obtained by reacting HB 9319 with radiolabeled extracts of FG cells.

The method follows that of Example 4(E) using HB 9319 in place of HB 9318. The resulting pattern of migration is shown in FIG. 2.

E. TREATMENT WITH GLYCOLYTIC ENZYMES

The antigen recognized by HB 9319 is isolated by immunoprecipitation of radiolabeled cell lysates. The immunoprecipitates are treated with a variety of exoglycolytic and endoglycolytic enzymes. After treatment the apparent mobility of the precipitated antigens is determined in a SDS-PAGE system. The glycolytic enzymes characteristically modify the apparent molecular weight of the HB 9319 antigens, by removing discrete portions of O-linked or N-linked glycans. The results obtained can be schematically summarized as follows:

| Enzyme | Apparent MW After Treatment |
|---|---|
| Endo H | 140 kd |
| NA | 135 kd |
| Endo N | 140 kd |

F. BINDING TO LECTINS

The method follows that of Example 4(G), using HB 9319 in place of HB 9318. When radiolabeled lysates were preabsorbed with lentil lectin-agarose beads, the antigens reactive with HB 9319 were removed. When they were preabsorbed with wheat germ agglutinin-agarose beads, the antigens were not removed. Removal of antigen was shown by immunoprecipitation of bead supernatant, followed by SDS-PAGE. Therefore, the antigen reactive with HB 9319 characteristically binds to lentil lectin, but not to wheat germ agglutinin.

G. BIOSYNTHESIS OF HB 9319 ANTIGEN

The method is as described in Example 4(I). Pulse-chase biosynthetic studies revealed the presence of a precursor molecule of 120 kD after a 10 minute pulse with [35S]-methionine. At the 15 minute time point of chase small amounts of the 140 kda HB 9319 antigen were also visible. Both of these molecules were observed to be present until 60 minutes after chase. However, only the 140 kd molecule was detectable at 4 hours after chase until 20 hours after chase. Thus, the 120 kd component serves as a precursor for the 140 kd component of the HB 9319 antigen.

V. EXAMPLES OF USES FOR THE PRESENT INVENTION

EXAMPLE 6

THERAPEUTIC TREATMENT OF HPC

Patients determined to have HPC are treated with monoclonal antibodies reactive with HPC cells and conjugated with a toxin such as ricin, or any cytotoxic drug. The monoclonal antibody conjugates are administered (intravenously, intramuscularly, intraperitoneally, or the like, in a physiologically acceptable carrier solution, such as phosphate buffered saline. The dosage is determined by the body weight of the host, it preferably being in the range of about 0.1 mg/kg to about 40 mg/kg body weight, and usually about 1 mg/kg to about 10 mg/kg of host body weight. Alternatively, the dosage is established by evaluating the extent of the tumor as by quantitatively standardized ELISA, radioimaging or other methods. Treatment is repeated at intervals as necessary, to effect enhancement of the host's ability to recover from the infection.

EXAMPLE 7

IMAGING OF HPC TUMOR

Monoclonal antibodies reactive with HPC cells are utilized to determine the location and extent of HPC by methods well-known in the art, for example, Larson et al. (1983) *J. Clinical Investigation* 72:2101, which is incorporated by reference. Monoclonal antibodies are preferably radiolabeled by radioiodination or by other radiolabeling techniques well known in the art, such as chelation using a chelating agent such as diethylenetriaminepenta-acetic acid (DTPA); or are otherwise labeled, such as with agents having paramagnetic properties, with chemiluminescent substrates, or with components of an enzymatic reaction. The radiolabeled monoclonal antibodies are purified and formulated for pharmaceutical use. A solution of the labeled monoclonal antibodies in a carrier, for example in phosphate buffered saline, is injected intravenously into a host. The appropriate dose is in the range of about 100 μg to 50 mg. Time is permitted for the antibodies to migrate to regions of the body having concentrations of cells with antigenic determinants reactive therewith. Concentrations of radioisotypes in certain tissues are determined or may be mapped either by techniques of whole body imaging which are well-known in the art, (See, for example, Rainsbury et al. (1983) *Lancet* October 22, 934 (1983)) which is incorporated by reference, or by evaluating biopsied tissue or extracted body fluid using a scintillation counter. Where non-radioactive labels are used, other appropriate monitoring means are employed, such as a detector of nuclear magnetic resonance or a spectrophotometer. Areas of high radiation levels are indicative of the presence of cells such as HPC, having the cell surface markers of the present invention.

The foregoing examples provide specific embodiments of the present invention, other embodiments being readily within the skill in the art. Thus, the scope of the present invention is defined by the following claims without limitation to the foregoing examples.

We claim:

1. An isolated human heterodimeric protein complex of 400 kd by SDS PAGE or 500 kd by gel filtration which immunoreacts with Mab HB 9318 and that consists essentially of:
   a) a first glycopeptide characterized by having apparent molecular weight in SDS-PAGE under reducing conditions of about 205 kd and under non-reducing conditions of about 190 kd, and glycosidase susceptibility to treatment with endo F and neuraminidase but not endo H, said first glycopeptide including the amino acid residue sequence N-R-C-K-K-A-P-V-K-S-C-T-E-C-V;

b) a second glycopeptide characterized by having apparent molecular weight in SDS-PAGE under reducing conditions of about 125 kd and under non-reducing conditions of about 150 kd, and glycosidase susceptibility to treatment with endo F, endo H and neuraminidase, said second glycopeptide including the amino acid residue sequence F-N-L-D-T-R-E-D-N-V-I-R-K-Y-G-D-P-G-S-L-F; and the deglycosylated and partially deglycosylated forms of said complex.

* * * * *

UNITED STATES PATENT AND TRADEMARK OFFICE
CERTIFICATE OF CORRECTION

PATENT NO. : 5,344,919

DATED : September 6, 1994

INVENTOR(S) : Quaranta, et al.

It is certified that error appears in the above-identified patent and that said Letters Patent is hereby corrected as shown below:

In Column 1, line 4, insert:

--This invention was made with government support under Contract No. 1R01 CA47858 awarded by the National Institutes of Health. The government has certain rights in the invention.--

Signed and Sealed this

Twenty-eighth Day of May, 1996

Attest:

BRUCE LEHMAN

Attesting Officer

Commissioner of Patents and Trademarks